(12) United States Patent
Gottschalk

(10) Patent No.: US 11,839,627 B2
(45) Date of Patent: *Dec. 12, 2023

(54) COMPOSITIONS AND METHODS FOR TREATING PRURITIS ANI AND ANAL FISSURES

(71) Applicant: Peter John Gottschalk, Maple Plain, MN (US)

(72) Inventor: Peter John Gottschalk, Maple Plain, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/102,014

(22) Filed: Jan. 26, 2023

(65) Prior Publication Data

US 2023/0165894 A1   Jun. 1, 2023

Related U.S. Application Data

(63) Continuation-in-part of application No. 15/717,869, filed on Sep. 27, 2017.

(51) Int. Cl.
| | |
|---|---|
| *A61K 8/26* | (2006.01) |
| *A61K 33/08* | (2006.01) |
| *A61K 47/06* | (2006.01) |
| *A61K 36/534* | (2006.01) |
| *A61K 33/30* | (2006.01) |

(52) U.S. Cl.
CPC ............ *A61K 33/08* (2013.01); *A61K 33/30* (2013.01); *A61K 36/534* (2013.01); *A61K 47/06* (2013.01)

(58) Field of Classification Search
None
See application file for complete search history.

(56) References Cited

U.S. PATENT DOCUMENTS

| | | | | |
|---|---|---|---|---|
| 4,797,392 A | * | 1/1989 | Chernomorsky | ...... A61K 31/40 514/410 |
| 2017/0128392 A1 | * | 5/2017 | Maurello | ............... A61K 36/87 |

FOREIGN PATENT DOCUMENTS

JP    4549006 B2 *  9/2010

* cited by examiner

*Primary Examiner* — Susan T Tran
(74) *Attorney, Agent, or Firm* — Italia IP; James A. Italia

(57) ABSTRACT

Compositions and methods for the treatment of pruritic ani and anal fissures are described. The compositions include one or more of Calamine (USP) or zinc oxide (ZnO), aluminum hydroxide $(Al(OH)_3)$ or kaolin, glycerin, and menthol (or any compound which activates the menthol receptor (TRPM8)). The composition does not contain any hydrocarbon-based pharmaceutical carrier such as petroleum jelly, white petrolatum, mineral oil, hard paraffin, soft paraffin, microcrystalline wax, ceresine, or hard fats. Methods of treating pruritic ani and anal fissures by topical application(s) of the compositions to affected perianal or anal epidermis are also described.

18 Claims, No Drawings

COMPOSITIONS AND METHODS FOR TREATING PRURITIS ANI AND ANAL FISSURES

CROSS-REFERENCE TO RELATED APPLICATION

This application is a Continuation-in-Part of U.S. Non-Provisional Utility application Ser. No. 15/717,869 filed Sep. 27, 2017, the contents of which are incorporated by this reference.

BACKGROUND OF THE INVENTION

Field of the Invention

The present invention relates to novel compositions and methods for the treatment of pruritis ani and anal fissures. More particularly, embodiments of the present invention relate to novel compositions comprising one or more of Calamine (USP) or zinc oxide, aluminum hydroxide (Al(OH)$_3$), kaolin, glycerin, and menthol (or any compound which activates the menthol receptor) as well as methods of treating pruritic ani and anal fissures by topical application(s) of the compositions to affected perianal or anal epidermis. In particular novel embodiments, the composition does not contain a hydrocarbon-based pharmaceutical carrier such as petroleum jelly, white petrolatum, mineral oil, hard paraffin, soft paraffin, microcrystalline wax, ceresine, or any hard fats.

Description of Related Art

Pruritis ani is a condition in which the perianal skin tends to itch. This can be due to numerous causes, the majority of which are idiopathic, and the remainder due to poor hygiene. Potential causes include inflammatory bowel disease, bacterial infections, skin disorders, food and dietary supplements, and skin irritants which may include local anesthetics, ointments, soaps, and sanitary wipes (see Parswa Ansari, MD, "Pruritus Ani (Anal Itching)", Merck Manuals, October 2016, available on the Internet). Thus, many 'treatments' for this irritating condition paradoxically tend to worsen symptoms.

An anal fissure is defined as an acute longitudinal tear or a chronic ovoid ulcer in the squamous epithelium of the anal canal (see Parswa Ansari, MD, "Anal Fissure (Fissure in Ano; Anal Ulcer)", Merck Manuals, October 2016, available on the Internet). Anal fissures may cause severe pain particularly upon or after defecation, and may bleed. Treatments for this condition may include local hygiene, stool softeners, topical medications, and sometimes botulinum toxin injection or a surgery. According to the Mayo Clinic website, potential causes of anal fissures include passing large or hard stools, constipation and straining during bowel movements, chronic diarrhea, inflammation of the anorectal area, which may be caused by Crohn's disease or another inflammatory bowel disease, and childbirth (see "Anal fissure-Symptoms and Causes", available on the Mayo Clinic website).

Efforts have been made to treat both of these conditions through topical administration of pharmacologic agents such as anesthetics and anti-inflammatories. However, such pharmacological agents have inherent issues associated with them such as side effects and the development of tolerance, and the fact that these are not effective for many people with these conditions.

Examples of efforts in this area and related areas include those described in U.S. Pat. Nos. 6,242,010; 6,495,602; 9,072,747; and U.S. Patent Publication No. 20060034825; yet, as with any art there is a need for improvements.

SUMMARY OF THE INVENTION

Embodiments of the invention comprise compositions and methods for the treatment of pruritis ani and anal fissures. Active ingredients of the composition include Calamine (zinc oxide and 0.5% ferric oxide) or zinc oxide (ZnO), aluminum hydroxide (Al(OH)$_3$) or kaolin, and glycerin. Menthol or other menthol receptor agonist in one or more pharmaceutically acceptable carriers may also be included. Note that aluminum hydroxide may also be referred to as "aluminum hydroxide gel" and as such, the inventor understands that these terms are synonymous and interchangeable. Embodiments include methods of treating pruritis ani and anal fissures comprising topical application of the compositions to affected areas (e.g perianal or anal skin).

Aspect 1. A composition comprising aluminum hydroxide or kaolin, zinc oxide or Calamine, glycerin, and optionally menthol and one or more pharmaceutically acceptable carriers, wherein the composition does not contain a hydrocarbon-based pharmaceutical carrier such as petroleum jelly, white petrolatum, mineral oil, hard paraffin, soft paraffin, microcrystalline wax, ceresine, or any hard fats.

Aspect 2. The composition of Aspect 1, wherein the composition takes the form of a topical cream.

Aspect 3. The composition of any preceding Aspect, wherein the composition has a viscosity in the range of 30,000 centipoise to 200,000 centipoise.

Aspect 4. The composition of any preceding Aspect, wherein the composition has a pH in the range of 7.1-9.0.

Aspect 5. The composition of any preceding Aspect, wherein the composition does not comprise any hydrocarbon-based pharmaceutical carrier or hard fats.

Aspect 6. The composition of any preceding Aspect, wherein the composition does not comprise petroleum jelly, white petrolatum, mineral oil, hard paraffin, soft paraffin, microcrystalline wax, or ceresine.

Aspect 7. The composition of any preceding Aspect, wherein the composition further comprises a menthol receptor (TRPM8) agonist.

Aspect 8. The composition of any preceding Aspect, wherein the menthol-receptor agonist is menthol.

Aspect 9. The composition of any preceding Aspect, wherein: aluminum hydroxide or kaolin is present in the composition at a concentration in the range of 12.5-25% (w/w); and zinc oxide or Calamine is present in a concentration in the range of 12.5-25% (w/w).

Aspect 10. The composition of any preceding Aspect, wherein: aluminum hydroxide or kaolin is present in the composition at a concentration in the range of 12.5-25% (w/w); zinc oxide is present in the composition at a concentration in the range of 12.5-25% (w/w); glycerin at a concentration range of 10-45%.

Aspect 11. The composition of any preceding Aspect, further comprising menthol or any menthol-receptor (TRPM8) agonist is present at a concentration of 0.1-1.0% (w/w).

Aspect 12. A composition comprising: aluminum hydroxide or kaolin at a concentration in the range of 12.5-25% (w/w); zinc oxide or Calamine at a concentration in the range of 12.5-25% (w/w); and menthol or menthol-receptor (TRPM8) agonist at a concentration of 0.1-1.0% (w/w); and one or more pharmaceutically acceptable carriers; wherein:

the composition does not comprise petroleum jelly, white petrolatum, mineral oil, hard paraffin, soft paraffin, microcrystalline wax, ceresine, or any hard fats; and the composition takes the form of a topical cream with a viscosity in the range of 30,000 centipoise to 200,000 centipoise.

Aspect 13. The composition of Aspect 14, further comprising glycerin.

Aspect 14. The composition of any preceding Aspect, wherein glycerin is present in the composition at a concentration in the range of 10-45% (w/w).

Aspect 15. The composition of any preceding Aspect, wherein the one or more pharmaceutically acceptable carriers comprise Acrylates/C 10-30 Alkyl Acrylate Crosspolymer, Dimethicone/Vinyl Dimethicone Crosspolymer, Cetearly Alcohol, Magnesium Aluminum Silicate, Deionized Water, Isopropyl Palmitate, Phenoxyethanol (Phenoxetol™), Polysorbate 20, Propylene Glycol, SD Alcohol, or Stearyl Alcohol.

Aspect 16. A method for treating pruritus ani or anal fissures comprising: applying an effective amount of the composition of claim 2 to the perianal or anal skin of a patient in need thereof.

Aspect 17. The method of Aspect 18, which is a method of treating pruritis ani, comprising: cleaning and drying the perianal or anal skin of the patient; and applying the composition to the perianal or anal skin when itching occurs.

Aspect 18. The method of Aspect 18, which is a method of treating anal fissures, comprising: applying the composition to the perianal or anal skin of the patient twice a day.

Aspect 19. A composition comprising calamine or zinc oxide, kaolin or aluminum hydroxide, and one or more pharmaceutically acceptable carriers.

Aspect 20. The composition of Aspect 21, wherein the composition takes the form of a topical cream.

Aspect 21. The composition of any preceding Aspect, wherein the composition has a viscosity in the range of 30,000 centipoise to 200,000 centipoise.

Aspect 22. The composition of any preceding Aspect, wherein the composition has a pH in the range of 7.1-9.0.

Aspect 23. The composition of any preceding Aspect, wherein the composition does not comprise any hydrocarbon-based or hard fat based pharmaceutical carrier.

Aspect 24. The composition of any preceding Aspect, wherein the composition does not comprise petroleum jelly, white petrolatum, mineral oil, hard paraffin, soft paraffin, microcrystalline wax, or ceresine.

Aspect 25. The composition of any preceding Aspect, wherein the composition further comprises a menthol receptor (TRPM8) agonist.

Aspect 26. The composition of any preceding Aspect, wherein the menthol-receptor agonist is menthol.

Aspect 27. A method for treating pruritus ani or anal fissures comprising: applying an effective amount of the composition of Aspect 22 to the perianal or anal skin of a patient in need thereof.

Aspect 28. The method of Aspect 38, which is a method of treating pruritis ani, comprising: cleaning and drying the perianal or anal skin of the patient; and applying the composition to the perianal or anal skin when itching occurs.

Aspect 29. The method of Aspect 38, which is a method of treating anal fissures, comprising: applying the composition to the perianal or anal skin of the patient twice a day.

Additional embodiments and aspects of the invention will be apparent in the foregoing Detailed Description.

DETAILED DESCRIPTION OF VARIOUS EMBODIMENTS OF THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

As used herein, the term "about" is understood as within a range of normal tolerance in the art, for example within 2 standard deviations of the mean. The term "about" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about".

As used herein, concentrations expressed as "% w/w" or "% (w/w)" indicates % weight per weight—which is known in the art as a concentration based on the weight of the individual component of the composition divided by the total weight of the composition. Unless explicitly stated otherwise, all concentrations disclosed herein are intended to be % weight per weight.

As used herein, the term "patient" or "patient in need thereof" refers to a human or animal suffering from pruritis ani (also known as perianal pruritis), anal fissures, or related conditions such as hemorrhoids. The animal patient may be any animal, such as a mammal, subject to pruritis ani and/or anal fissures and/or related conditions as recognized in the veterinary arts, including domestic animals, farm animals, exotic animals, zoo animals, and the like.

As used herein, the term "affected area" refers to the perianal or anal skin of a human or animal patient. The skin can include the epidermis as well as exposed sub-epidermal layers in the case of fissures.

As used herein, "Pranicura" refers to a particular embodiment of a composition of the invention demonstrated in the Example.

As used herein, "Pranicura Treatment" refers to a particular embodiment of a method of the invention demonstrated in the Example.

Embodiments with kaolin or aluminum hydroxide (Al$(OH)_3$):

Embodiments of the present invention provide compositions and methods for the treatment of pruritus ani and anal fissures. Embodiments of compositions of the invention include a combination of one or more active ingredients comprising Calamine (USP) or zinc oxide (ZnO), aluminum hydroxide (Al$(OH)_3$) or kaolin, glycerin, and menthol, in one or more pharmaceutically acceptable carriers. Kaolin is an odorless white to yellowish or grayish powder. Contains mainly the clay mineral kaolinite (Al2O3(SiO2)2(H2O)2), a hydrous aluminosilicate. Kaolinite has mp 740-1785° C. and density 2.65 g/cm3. Kaoline is insoluble in water but darkens and develops a earthy odor when wet. Kaolin is a mixture consisting principally of the mineral kaolinite and containing varying amounts of other minerals such as muscovite, quartz, feldspar, and anatase. Calamine USP (CAS Registry No.: 8011-96-9) is a skin protectant (primarily comprising zinc oxide (ZnO)) and defends against bacteria. Glycerin (also known as glycerol, CAS Registry No.: 56-81-65) is a skin protectant. Menthol (including L-Menthol, CAS Registry No.: 2216-51-5, and DL-menthol, CAS Registry No. 1490-04-6 and CAS Registry No. 89-78-1) is an analgesic and anti-itch compound and aluminum hydroxide (CAS Registry No. 21645-51-2) neutralizes acids. Embodiments of the invention provide these active ingredients (as well as inactive ingredients) in the compositions according to standards defined in the United States Pharmacopeia-National Formulary (USP-NF) as well as the FDA Anal Ointment Monograph (21 CFR part 346), each of which is incorporated herein by reference.

In embodiments with aluminum hydroxide or kaolin, Calamine or zinc oxide is present in the composition as an active ingredient at a concentration 12.5-25% (w/w). As used herein, "Calamine" refers to a pink, water-insoluble powder consisting of zinc oxide (ZnO) and about 0.5 percent ferric oxide ($Fe_2O_3$). In embodiments, pure zinc oxide (i.e. with no ferric oxide) substitutes for Calamine in the composition at the above concentrations. Further, other embodiments may include other forms of zinc instead of zinc oxide, such as zinc sulfate, zinc chloride, zinc acetate, and the like.

In embodiments, aluminum hydroxide or kaolin is present in the composition as an active ingredient at a concentration of 12.5-50% (w/w)

Glycerin (also known as glycerol, CAS Registry No.: 56-81-65) is a skin protectant. Menthol (including L-Menthol, CAS Registry No.: 2216-51-5, and DL-menthol, CAS Registry No. 1490-04-6 and CAS Registry No. 89-78-1) is an analgesic and anti-itch compound and aluminum hydroxide (CAS Registry No. 21645-51-2) neutralizes acids. Embodiments of the invention provide these active ingredients (as well as inactive ingredients) in the compositions according to standards defined in the United States Pharmacopeia-National Formulary (USP-NF) as well as the FDA Anal Ointment Monograph (21 CFR part 346), each of which is incorporated herein by reference.

In embodiments with either aluminum hydroxide or kaolin, menthol is present in the composition as an active ingredient at a concentration of about 0.1-1% by weight (w/w). In a preferred embodiment, menthol is present in the composition at a concentration of about 1% (w/w). Further, embodiments of the composition may include any natural or synthetic derivatives or isomers of menthol at the above concentrations. Examples of isomers of menthol include (+)-menthol, (−)-menthol, (+)-isomenthol, (−)-isomenthol, (+)-neomenthol, (−)-neomenthol, (+)-neoisomenthol, and (−)-neoisomenthol. Examples of derivatives of menthol include those described in U.S. Patent Application Publication No. US 20120014884 and U.S. Pat. No. 6,566,545. Other compounds that may be used in substitution of menthol at the above concentrations include phenol, camphor, thymol, eugenol, carvone, 'coolant agent 10' (also known as 3-((L-Menthyl)oxy)propane-1,2-diol), and others described in the literature (see Eccles R1, "Menthol and related cooling compounds", J Pharm Pharmacol. 1994 August; 46(8):618-30). In another embodiment, any compound that activates or acts as an agonist of the physiological receptor for menthol (TRPM8/CMR1, see Bautista D. M., "The menthol receptor TRPM8 is the principal detector of environmental cold", Nature 448, 204-208 (12 Jul. 2007)) may be used in the composition at the above concentrations. Such compounds may include linalool, geraniol, hydroxy-citronellal, WS-3, WS-23, Frescolat MGA, Frescolat ML, PMD 38, Coolact P, and Coolant Agent 10 (see Behrendt H J, Germann T, Gillen C, Hatt H, Jostock R (February 2004). "Characterization of the mouse cold-menthol receptor TRPM8 and vanilloid receptor type-1 VR1 using a fluorometric imaging plate reader (FLIPR) assay". Br. J. Pharmacol. 141 (4): 737-45).

Inactive ingredients of the compositions with either aluminum hydroxide or kaolin can include, but may not be limited to, one or more of pharmaceutically-acceptable carriers which are well known in the pharmaceutical arts. Non-limiting examples of such carriers include such vehicles as water; organic solvents, alcohols, lower alcohols that are readily capable of evaporating from the skin, ethanol, glycols, glycerin, aliphatic alcohols, mixtures of water and organic solvents, mixtures of water and alcohol, mixtures of organic solvents such as alcohol and glycerin, glycerols, phosphoglycerides, sphingolipids, waxes, DMSO, protein-based materials such as collagen and gelatin, volatile and/or non-volatile silicon-based materials, cyclomethicone, dimethiconol, dimethicone copolyol (Dow Corning, Midland, MI, USA), release vehicles such as microsponges and polymer matrices, suspending agents, emulsifying agents, and other vehicles and vehicle components that are suitable for administration to the anal or perianal region, as well as mixtures of topical vehicle components as identified above or otherwise known to the art.

In more particular embodiments with either aluminum hydroxide or kaolin, the inactive ingredients can include one or more pharmaceutically acceptable carriers (or other ingredients) such as Acrylates/C 10-30 Alkyl Acrylate Crosspolymer, Dimethicone/Vinyl Dimethicone Crosspolymer, Cetearly Alcohol, Magnesium Aluminum Silicate, Deionized Water, Isopropyl Palmitate, Phenoxyethanol (Phenoxetol™), Polysorbate 20, Propylene Glycol, SD Alcohol, and Stearyl Alcohol. The inactive ingredients may also include an emulsifier such as Pemulen™ TR-2, a polymeric emulsifier which is a high molecular weight, crosslinked copolymer of acrylic acid and a hydrophobic C10-30 alkyl acrylate co-monomer. The inactive ingredients comprise, by weight % (w/w), the remainder of the composition, and together may be present in an amount ranging from 10-90%, 25-75%, 40-60%, 45-55% (w/w) of the composition, including 15%, 20%, 25%, 30%, 35%, 40%, 45%, 50%, 55%, 60%, 65%, 70%, 75%, 80%, 85%, or 90% (w/w), or at any range including or encompassing these values.

Further embodiments of the composition with either aluminum hydroxide or kaolin are formulated so that the composition does not contain a hydrocarbon-based pharmaceutical carrier or hard fats such as petroleum jelly, white petrolatum, mineral oil, hard paraffin, soft paraffin, microcrystalline wax, ceresine and the like.

In additional embodiments with either aluminum hydroxide or kaolin, the compositions are formulated so that they do not contain any corticosteroids such as bethamethasone, prednisone, prednisolone, triamcinolone, methylprednisolone, dexamethasone, hydrocortisone, clobetasol propionate, betamethasone dipropionate, halobetasol propionate, diflorasone diacetate, fluocinonide, halcinonide, amcinonide, desoximetasone, mometasone furoate, fluticasone propionate, betamethasone dipropionate, halometasone, fluocinolone acetonide, flurandrenolide, fluticasone, desonide, fluocinolone, alclometasone, and the like.

Embodiments of the composition with aluminum hydroxide or kaolin may have a viscosity in the range of 30,000 to 200,000 centipoise, more preferably at least 90,000 centipoise, still more preferably 100,000 to 170,000 centipoise. By way of illustrative examples, a composition of about 1 centipoise has the viscosity of water, a composition in the hundreds of centipoise has the viscosity of motor oil, a composition of about 1,000 centipoise has the viscosity of glycerin, a composition of about 50,000 centipoise has the viscosity of ketchup, a composition of about 150,000-200,000 centipoise has the viscosity of tomato paste or peanut butter. For further reference, petroleum jelly has a viscosity of around 64,000 centipoise. According to the U.S. Food and Drug Administration, lotions (such as Calamine lotion that is available over the counter) generally have a viscosity less than 30,000 centipoise, while creams have a viscosity greater than 30,000 centipoise (see https://www.fda.gov/ ohrms/dockets/ac/03/briefing/3926B1_01_F-FDA-Definitions%20of%20Dosage%20Forms%202-12-03.htm).

Embodiments of the composition with aluminum hydroxide or kaolin have a pH that is slightly alkaline such as in the range of 7.1-9.0, including 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, and 9.0, and any range including or encompassing these values such as 8.0-8.9, 7.5-8.5, 7.7-8.8, and so on.

Embodiments of the composition with kaolin have a pH in the range of 6.8-8.2, including 6.9, 7.0, 7.1, 7.2, 7.3, 7.4, 7.5, 7.6, 7.7, 7.8, 7.9, 8.0, 8.1. More preferably, the pH range is 7.0 to 8.0.

Exemplary Formulation with Aluminum Hydroxide or Kaolin and Calamine or Zinc Oxide:

In one embodiment with kaolin, preparation of the composition may comprise the following steps. Individual components of the composition may be compounded in "phases" (i.e. Phase I-Phase VI) according to the table below, which shows an exemplary formulation.

TABLE I

Exemplary Formulation with Aluminum Hydroxide or Kaolin and Calamine or Zinc Oxide

| Phase | Raw Material | % by Weight (w/w) |
|---|---|---|
| Phase I | Water | 11.50 |
| | Pemulen ™ TR-2 | 0.30 |
| Phase II | Water | 12.20 |
| | Polysorbate 20 | 0.5 |
| | Phenoxetol ™ | 1.0 |
| Phase III | Glycerin | 25.0 |
| | Calamine or Zinc Oxide | 12.5 |
| Phase IV | Propylene Glycol, USP | 10.0 |
| | Isopropyl Palmitate | 2.0 |
| | Aluminum Hydroxide or Kaolin | 12.5 |
| Phase V | Stearyl Alcohol | 2.75 |
| | Cetearyl Alcohol (70/30) | 4.75 |
| Phase VI | SD Alcohol 40/40-2, 190 Proof | 4.0 |
| | L-Menthol, USP | 1.0 |

Acceptable ranges of the above constituents may include +/−10, 15, 20, 25, 50, 75, 80, 90, 95, 96, 97, 98, 99, 99.9, 99.99, or 100% of the above values in Table II.

The following described an exemplary procedure for the mixing/compound process to prepare an embodiment of the composition of the invention, according to the above Phases:

1. Ensure the mixing/compounding process areas, work surfaces, containers, mixers, equipment and instruments to be used in this process have been cleaned and sanitized.
2. Weigh & Combine Phase I in a container. Mix until paste formed is fully hydrated.
3. Weigh Phase II Water in final mixing tank. Add additional ingredients one at a time with mixing.
4. Add Phase I paste to Phase II with mixing in main mixing tank. Ensure mixing continues until there are no visible clumps. Begin heating up to at least 60-65° C.
5. Weigh & Combine Phase III in a container. Mix until fully hydrated. Once fully hydrated, begin adding to main mixing tank. Maintain tank temp 60-65° C.
6. Combine Phase IV in a container. Mix until fully hydrated. Once fully hydrated, begin adding to main mixing tank. Maintain tank temp 60-65° C.
7. Combine Phase V in a hot bowl. Heat to 60-65° C. to melt. Mix for at least 5-10 minutes or until uniform.
8. Once both the main mixing tank and Phase V are at temperature, slowly add Phase V with mixing.
9. Continue mixing to thoroughly blend. Begin reducing heat and continue mixing.
10. Weigh & Mix Phase VI. Add Phase VI to the main batch when at 30° C. and continue mixing until at room temperature.

Additional embodiments of the invention include methods for treating pruritus ani and anal fissures. In embodiments, the methods comprise contacting the perianal or anal skin (e.g. epidermis) of a patient in need thereof with a composition of the present invention.

In embodiments, the composition is applied only as needed (e.g. during itching), or regularly (e.g. every day) at least once a day, including twice a day, 3 times a day, 4 times a day, 5 times a day, 6 times a day, 7 times a day, 8 times a day, 9 times a day, 10 times a day, or even more frequently. The composition can be applied after a bowel movement and/or during a need to scratch (itching). The composition is preferably applied after cleaning the affected area (such as with a non-medicated baby wipe) and drying.

A more particular embodiment of the methods of the invention is described below in the following Example, which provides detailed treatment protocols and patient instructions for using a composition of the invention. However, the Example should not be construed as limiting the invention in any way.

Treatment Examples

The Pranicura Treatment takes 1-5 weeks for the affected area to heal. The treatment incorporates an easy 5 step process. In embodiments, every step is extremely important. The Pranicura Treatment was developed through years of trial and error testing by patients (chronic anal itching/pruritus ani sufferers) to arrive at the right ointment and the right process to get relief from this condition. The inventors' theory of the cause of pruritus ani is an unknown bacterium ("the culprit") in the rectum that when it makes contact with the anal/perianal skin, it causes itching, irritation, fissures, hemorrhoids, and other anal problems. Therefore, there can't be a cure until the culprit is eliminated from the rectum because the skin constantly gets "re-infected" daily by bowel movements, mucous leakage, and passing gas. Logic then dictates that to stop the irritation from happening, the patient must remove the "culprit" whenever it is present (indicated by itching/burning of the affected area) and then treat the anal/perianal skin with Pranicura if removing the "culprit" isn't enough. This logical sequence is the basis of the Pranicura Treatment and it's proven correct as the inventors have attained an almost perfect success rate. The composition of the invention is not a cure, but it will end or relieve the patient's suffering. A cure would be eliminating the culprit so the patient will never itch again. The Pranicura Treatment (ointment and process) is a long-term solution. It is extremely difficult to accept for the patient to accept that they now have a lifelong affliction. However, the good news is that with the Pranicura Treatment the patient will only have to deal with this problem a few minutes each day. After the 1-5 week healing process, most people can go 1-3+ weeks between ointment applications. Worst case, they may need to apply ointment once every 2-5 days after the initial healing.

The 5-step Pranicura Treatment Patient Instructions:
1) When and how often? Never on a schedule such as every night before bed. Leave the affected area alone as much as possible. Perform steps 2 thru 4 if one of the following occurs: After every bowel movement and every time the patient feels the need to scratch.
2) Clean with a non-medicated, non-alcohol, generic baby wipe, until no color shows on the wipe. Do not use any wipe that is medicated such as Tucks or Prep H wipes. Wipes with aloe are just fine.
3) Pat dry with toilet tissue. Do not scratch with the toilet tissue. Just pat dry thoroughly. The best success will be reached if the affected area is dry.
4) Wait and if the itch is gone, then do NOT apply ointment. Relief! The best thing for the affected area is nothing, if possible. The goal is to apply ointment as few times as possible! Pranicura is safe to use daily, but the fewer times the ointment is applied or the affected area is touched, the better it will be.
5) If the itch is still there after step 4, ointment can be applied. Apply Pranicura with a finger and rub/scratch with no fingernails until the itch is satisfied. It can be applied to the inner rim of the anus but not inserted deep into the rectum. This is the only time the affected area should be scratched. It is a lubricated scratch which minimizes skin damage. (Scratching with fingernails causes skin damage and will extend healing time dramatically.) Some will notice that when Pranicura is applied the itch will increase. Pranicura works by over-stimulating nerve endings so it's critical to rub it in until the nerves go dead and the itch is satisfied.

The following are Pranicura Treatment Instructions for those with NO Itching. (Fissures or Hemorrhoids with no itching.)

Depending on the severity of the fissure, the patient can expect a healing time of 1-3 MONTHS. Here is a course of action for the patient to heal and stay healed:

1) The patient should apply Pranicura twice a day. The patient should not use any other over the counter products (Except for Recticare lidocaine cream if the patient is in severe pain. They should try to stop using it as soon as possible as it may lengthen the fissure healing time.) No oils and nothing with petrolatum. The present inventors believe that all of them weaken tissues and can worsen the condition. If the patient has a prescription ointment from the doctor that they inject into the rectum . . . then they should use that as directed in addition to Pranicura. Pranicura will help do the healing from the anus inward and the doctor's prescription may help with healing and pain internally. Pranicura will not help with pain relief. It is unique in its ability to stay put and attach itself to the hot moist skin area of the anus/anal area and help with healing. The patient should not apply Pranicura more than twice a day. The ideal scenario is to apply Pranicura once in the morning after a bowel movement and then once in the evening after a 10 minute warm bath. See below.
2) After every bowel movement, the patient should wipe once or twice with toilet tissue to remove most of the feces, and then clean with a baby wipe until there is no color showing on the wipe. Then pat dry. The patient should make sure the affected area is very dry and then apply Pranicura on the anus and just inside the inner rim of the anus but NOT deep inside the rectum. If the patient has several bowel movements a day . . . then they should substitute Desiten original diaper rash ointment for Pranicura. The inventors don't want Pranicura to be applied more than twice a day so if they have more than one bowel movement a day then they should apply Desiten. (Or Sudocrem antiseptic ointment. Or any other inexpensive zinc oxide based diaper rash ointment. The patient should ask their pharmacist for a recommendation).
3) Take 10 minute warm soaks in the tub with Epsom salts (per the directions on their box) several times a week. Remove Pranicura prior to this soak with a baby wipe and then pat dry thoroughly with toilet tissue or use a fan or hair dryer on the cold setting to really dry the affected area. Then apply Pranicura.
4) If Pranicura burns too much when applied then Desiten should be substituted (or another alternative, see #2 above) for Pranicura until the affected area heals enough to handle Pranicura.
5) After the patient heals, they should slowly reduce the number of applications. Reduce applications to once a day after a bowel movement for a couple of weeks, and then once every few days, and then according to need to keep fissures from reoccurring. But the patient should continue to clean with a baby wipe and pat dry with toilet tissue after bowel movements daily for life. And the patient should do the same whenever they feel irritation at the affected area. The patient should apply Pranicura only when the affected area is still irritated after they pat dry.

If constipation is an issue, the inventors suggest magnesium supplements (make sure the patient is not allergic) in the amount that works for the patient. Generally that is 250-500 mgs.

Is the patient in a lot of pain for a long time after a bowel movement? They need to know that no matter what they do, it will take 1-3 months to heal a severe fissure. Pain lasting hours after a bowel movement may potentially only be healed with surgery, and the recovery time after that is 1-3 months as well. The patient must see a colon/rectal specialist if this is them. The inventors have told many people who are in pain for hours after a bowel movement to check with their doctors and if appropriate schedule surgery 3 months out and give our process a try. If the Pranicura treatment combined with the doctor's internal anal injected prescriptions fail . . . then surgery may be the patient's best option. Many people have reported to the inventors that multiple Botox injections have failed them, but the inventors have not heard from anyone that surgery has failed and they needed to find something else. Therefore the inventors' opinion is that surgery is a high success option . . . but the inventors recommend the Pranicura treatment to keep fissures from re-occurring. It's the inventors' theory that the same culprit (a bacteria in the rectum/feces) that causes pruritus ani, causes all anal irritation and problems. In addition, the inventors believe ointments containing petrolatum/petroleum jelly weaken skin tissues and exacerbates anal fissures causing them to get worse. Small fissures turn into severe fissures with consistent use of petrolatum ointments (which is in almost every ointment!) . . . that's the inventors' theory. And it's possible that once they get so bad that a person is in pain for hours after a bowel movement, that surgery might be the only option. But since the recovery from that surgery is horrible and takes 6-12 weeks, it's worth a few months of trying to heal "somewhat naturally" before going to the last resort of surgery. And just because the patient heals the fissure now, what is going to prevent more fissures from happening in the future? Many people report to the inventors that they have suffered for years on and off. The Pranicura treatment can prevent them from re-occurring and/or help heal them early so they don't become a major pain problem.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A composition for treating pruritus ani or anal fissures comprising:
   aluminum hydroxide or kaolin at a concentration in the range of 12.5-50% (w/w);
   zinc oxide or 95.5% zinc oxide with 0.5% ferric oxide (w/w) at a concentration in the range of 12.5-25% (w/w);
   glycerin at a concentration in the range of 10-45% (w/w); and
   one or more pharmaceutically acceptable carriers;
   wherein the total of the aluminum hydroxide or kaolin, zinc oxide or 95.5% zinc oxide with 0.5% ferric oxide (w/w), and glycerin is present in the composition at a concentration of about 50% (w/w) based on the composition;
   wherein the composition does not comprise a hydrocarbon-based pharmaceutical carrier; and
   wherein the composition does not comprise any corticosteroids; and
   the composition takes the form of a topical cream with a viscosity in the range of 30,000 centipoise to 200,000 centipoise.

2. The composition of claim 1, further comprising menthol, wherein the menthol is present in the composition at a concentration range of 0.1-1% (w/w).

3. The composition of claim 1, wherein the composition has a pH in the range of 7.0-8.2.

4. The composition of claim 1, wherein said zinc oxide or 95.5% zinc oxide with 0.5% ferric oxide (w/w) is present in the composition at a concentration of 12.5% (w/w).

5. The composition of claim 1, wherein said kaolin or aluminum hydroxide is present in the composition at a concentration of 12.5% (w/w).

6. The composition of claim 1, wherein the glycerin is present in the composition at a concentration of 25% (w/w).

7. The composition of claim 1, wherein the composition further comprises a menthol receptor (TRPM8) agonist.

8. The composition of claim 7, wherein the menthol-receptor (TRPM8) agonist is menthol.

9. The composition of claim 1, wherein:
   said zinc oxide or 95.5% zinc oxide with 0.5% ferric oxide (w/w) is present in the composition at a concentration of 12.5% (w/w);
   said kaolin or aluminum hydroxide is present in the composition at a concentration of 12.5% (w/w); and
   said glycerin is present in the composition at a concentration of 25% (w/w).

10. The composition of claim 9 further comprising menthol, wherein the menthol is present in the composition at a concentration range of 0.1-1% (w/w).

11. The composition of claim 10, wherein the menthol is present in the composition at a concentration of 1% (w/w).

12. A composition in a pharmaceutically acceptable carrier comprising:
   95.5% zinc oxide with 0.5% ferric oxide (w/w) at a concentration in the range of 12.5-25% (w/w);
   kaolin at a concentration in the range of 12.5-25% (w/w);
   glycerin at a concentration range of 10-45.0% (w/w); and
   one or more pharmaceutically acceptable carriers;
   wherein the total of the 95.5% zinc oxide with 0.5% ferric oxide (w/w), kaolin, and glycerin is present in the composition at a concentration of about 50% (w/w) based on the composition;
   wherein the composition does not comprise a hydrocarbon-based pharmaceutical carrier; and
   wherein the composition does not comprise any corticosteroids;
   and the composition takes the form of a topical cream with a viscosity in the range of 30,000 centipoise to 200,000 centipoise.

13. The composition of claim 12, wherein:
   said 95.5% zinc oxide with 0.5% ferric oxide (w/w) is present in the composition at a concentration of 12.5% (w/w);
   said kaolin is present in the composition at a concentration of 12.5% (w/w); and
   said glycerin is present in the composition at a concentration of 25% (w/w).

14. The composition of claim 13, further comprising menthol, wherein the menthol is present in the composition at a concentration of 1% (w/w).

15. The composition of claim 12, wherein the pharmaceutically acceptable carrier includes Acrylates/C 10-30 Alkyl Acrylate Crosspolymer, Dimethicone/Vinyl Dimethicone Crosspolymer, Cetearly Alcohol, Magnesium Aluminum Silicate, Deionized Water, Isopropyl Palmitate, Phenoxyethanol (Phenoxetol™), Polysorbate 20, Propylene Glycol, SD Alcohol, or Stearyl Alcohol.

16. A method for treating pruritus ani or anal fissures comprising:
   applying an effective amount of the composition of claim 1 to the perianal or anal skin of a patient in need thereof.

17. The method of claim 16, which is a method of treating pruritis ani, comprising:
   cleaning and drying the perianal or anal skin of the patient; and
   applying the composition to the perianal or anal skin when itching occurs.

18. The method of claim 16, which is a method of treating anal fissures, comprising:
   applying the composition to the perianal or anal skin of the patient twice a day.

* * * * *